United States Patent [19]

Topel et al.

[11] Patent Number: 4,958,621

[45] Date of Patent: Sep. 25, 1990

[54] ENDOSCOPIC ASPIRATION INSTRUMENT

[75] Inventors: Howard C. Topel, Deerfield, Ill.; Thomas L. Foster, Poland, Ind.

[73] Assignee: Vance Products Incorporated, Spencer, Ind.

[21] Appl. No.: 505,082

[22] Filed: Apr. 4, 1990

[51] Int. Cl.$^5$ .............................................. A61B 1/00
[52] U.S. Cl. ...................................................... 128/4
[58] Field of Search ....................................... 128/4, 6

[56] References Cited

U.S. PATENT DOCUMENTS

| 4,653,475 | 3/1987 | Seike et al. | 128/4 |
| 4,686,965 | 8/1987 | Bonnet et al. | 128/4 |
| 4,700,694 | 10/1987 | Shisido | 128/4 X |

OTHER PUBLICATIONS

American Surgical Instruments, Inc., "Nezhat–Dorsey Disposable Hydro-Dissection Trumpet Valve," 3 Sheets, received Mar. 19, 1990.
K. Semm, Pelviscopy Operative Guidelines, Kiel, F.R.G., 1988, pp. 53–54.
Storz The World of Endoscopy, Semm Instruments for Operative Pelviscopy, 4th Edition, Mar., 1987.

*Primary Examiner*—William H. Grieb
*Attorney, Agent, or Firm*—Richard J. Godlewski

[57] ABSTRACT

An endoscopic aspiration instrument suitable for use with a trocar sheath in laparoscopic surgical procedures is disclosed for aspirating fluid from an ovarian cyst without leakage of the fluid into the peritoneal cavity. The endoscopic instrument comprises a elongated suction tube member having a needle guide positioned within the passageway thereof. The suction tube and needle guide are connected at the proximal ends thereof with the use of a three access port connector. The first access port connects to the proximal end of the suction tube. The proximal end of the needle guide tube is extended through the first port and connected to the second port of the T-type connector. An aspiration needle is inserted through a sealing cap positioned over the second access port and into the passageway of the needle guide tube. A centering device comprising a sleeve and a plurality of radially extending arms is positioned about the distal end of the needle guide tube for centering the needle guide tube within the passageway of the suction tube. The centering device is also located a predetermined distance from the distal end of the suction tube for preventing the ovarian cyst from being drawn too far into the suction tube. The connector also includes a third side port for connection to suction equipment for providing a vacuum in the suction tube to engage the ovarian cyst.

20 Claims, No Drawings

ENDOSCOPIC ASPIRATION INSTRUMENT

TECHNICAL FIELD

This invention relates to medical instruments and particularly to an endoscopic medical instrument for aspirating biological tissue such as an ovarian cyst.

BACKGROUND OF THE INVENTION

A number of endoscopic medical and surgical instruments are available for aspirating fluid during a minimally invasive laparoscopic surgical procedure. One such endoscopic instrument is an aspiration needle for puncturing and aspirating fluid from, for example, an ovarian cyst. Another endoscopic instrument is an aspiration tube for aspirating fluid from the peritoneal cavity. One problem with the aspiration needle is that fluid leaks from around the shaft of the needle when the it punctures the cyst. Likewise, an aspiration tube allows fluid draining into the peritoneal cavity to come in contact with healthy tissue before and during removal. The problem of fluid leaking or draining into the peritoneal cavity is particularly heightened when the fluid contains malignant cells. The leakage of fluid with malignant cells to surrounding tissue significantly changes the morbidity and prognosis of the patient.

When a protein marker test produces a positive result indicating that an ovarian cyst is malignant, an invasive procedure is typically employed to remove the ovary and fallopian tube associated with the malignant cyst. As a result, the patient experiences a four to five day hospital stay with three to six weeks of post-operative recovery.

When the protein marker test produces a negative result indicating that the ovarian cyst may be benign, a minimally invasive, endoscopic close-chambered ovarian cyst removal technique is preferred. This minimally invasive procedure permits the patient to be discharged from the hospital within a 24 hour period with a normal post-operative recovery period lasting from three to five days. Typically, the patient is back to work or performing normal activity within five to eight days of this procedure. However, a negative protein marker test result is accurate only about 80% of the time. Consequently, the surgeon wants to prevent fluid leakage from the cyst. Should the ovarian cyst contain fluid having malignant cells, the morbidity and prognosis of the patient is significantly changed when the fluid is allowed to leak and come in contact with other healthy tissue within the peritoneal cavity. As a result, the morbidity and prognosis of the patient is typically worse than that of the invasive procedure where the malignant cells can be contained from further migration.

The prevention of fluid leakage to healthy tissue during endoscopic aspiration will not effect the morbidity or prognosis of the patient even though the fluid contains malignant cells. A pathological report of the aspirated fluid indicating that malignant cells are present would then indicate the need for the invasive surgical procedure where healthy tissue exposure to the malignant fluid is eliminated or contained. However, leakage of the malignant fluid during the minimally invasive procedure would significantly worsen the morbidity or prognosis of the patient even though the invasive procedure would be subsequently employed.

SUMMARY OF THE INVENTION

The foregoing problems are solved and a technical advance is achieved with an illustrative endoscopic instrument with particular applications to laparoscopic or pelviscopic procedures for aspirating a cyst without fluid leakage to other tissue within the peritoneal cavity. This endoscopic instrument is advantageously utilized as a pelviscopic instrument for aspirating an ovarian cyst during a close-chambered ovarian cyst drainage procedure. The endoscopic instrument comprises an elongated member such as a suction tube having a first longitudinal passageway extending between the distal and proximal ends of the tube, whereby the distal end of the tube is inserted through a trocar sheath. The proximal end includes first and second access ports of which the first access port is accessible to the passageway. A vacuum is applied to the first access port and passageway to engage and maintain purchase of the ovarian cyst with the distal end of the suction tube. The instrument also includes a positioning or centering device positioned within the suction tube passageway a predetermined distance from the distal end. The centering device has a passageway for receiving and centering an aspiration needle that is inserted advantageously through the second access port.

To further guide and center the aspiration needle, the endoscopic instrument includes a second elongated member such as a tubular needle guide having a second longitudinal passageway between distal and proximal ends thereof. The tubular needle guide is positioned within the suction tube passageway with the proximal end thereof being connected to the second access port. The second access port has access to the passageway of the tubular needle guide for inserting and guiding the aspiration needle therethrough.

A sealing cap is positioned over the second access port for maintaining purchase of the ovarian cyst when a vacuum is applied to the first access port of the suction tube. The aspiration needle is advantageously inserted through the sealing cap, second access port and extendable through the needle guide and beyond the distal end of the suction tube to puncture and aspirate the ovarian cyst without permitting any leakage of fluid within the peritoneal cavity.

Should any fluid leak from about the shaft of the aspiration needle, fluid from the cyst held in purchase with pelviscopic instrument for aspirating an ovarian cyst during a close-chambered ovarian cyst drainage procedure. The endoscopic instrument comprises an elongated member such as a suction tube having a first longitudinal passageway extending between the distal and proximal ends of the tube, whereby the distal end of the tube is inserted through a trocar sheath. The proximal end includes first and second access ports of which the first access port is accessible to the passageway. A vacuum is applied to the first access port and passageway to engage and maintain purchase of the ovarian cyst with the distal end of the suction tube. The instrument also includes a positioning or centering device positioned within the suction tube passageway a predetermined distance from the distal end. The centering device has a passageway for receiving and centering an aspiration needle that is inserted advantageously through the second access port.

To further guide and center the aspiration needle, the endoscopic instrument includes a second elongated member such as a tubular needle guide having a second longitudinal passageway between distal and proximal ends thereof. The tubular needle guide is positioned within the suction tube passageway with the proximal end thereof being connected to the second access port. The second access port has access to the passageway of the tubular needle guide for inserting and guiding the aspiration needle therethrough.

A sealing cap is positioned over the second access port for maintaining purchase of the ovarian cyst when a vacuum is applied to the first access port of the suction tube. The aspiration needle is advantageously inserted through the sealing cap, second access port and extendable through the needle guide and beyond the distal end of the suction tube to puncture and aspirate the ovarian cyst without permitting any leakage of fluid within the peritoneal cavity.

Should any fluid leak from about the shaft of the aspiration needle, fluid from the cyst held in purchase with the suction tube is aspirated through the suction tube and out of the first access port.

The instrument also includes a one-way check valve connected to the proximal end of the aspiration needle for preventing loss of purchase of the cyst within the suction tube as well as preventing any fluid within the aspiration needle from being drawn out of the distal end of the needle and through the suction tube. This also prevents loss of purchase of the suction tube with the cyst.

The outer surface of the suction tube includes a matte or non-glare finish for reducing, if not eliminating, the reflection of light from the suction tube during the endoscopic procedure. This significantly reduces annoying and fatiguing conditions to the attending physician.

Alternatively, the endoscopic instrument includes the suction tube with the first and second access ports at the proximal end thereof and the second elongated member, such as the tubular needle guide, positioned within the first passageway of the suction tube. The proximal end of the needle guide is connected to the second access port thereby allowing the second access port direct access to the passageway of the needle guide. The instrument further includes a positioning device attached about the proximal end of the needle guide tube and positioned within the first passageway of the suction tube a predetermined distance from the distal end thereof.

To facilitate reuse and cleaning, the endoscopic aspiration instrument utilizes a T-type connector having three access ports for interconnecting the suction tube and the tubular needle guide. Two ports of the connector are directly opposite from one another with the proximal end of the suction tube being connectable to the first port. The second or side port has access through the connector and to the passageway of the suction tube. The second elongated member is positioned through the first port and connected to the third port directly opposite therefrom. The passageway of the elongated tubular needle guide is accessible through this third port.

The instrument further includes a positioning or centering device attached about the distal end of the tubular needle guide which is positionable within the passageway of the suction tube when connected to the three port connector. The positioning device includes a sleeve and a plurality of arms extending radially therefrom and toward the inner surface of the suction tube. The positioning device is advantageously positioned a predetermined distance from the distal end of the suction tube to prevent the ovarian cyst from being drawn too far into the suction tube.

Similarly, the alternative endoscopic instrument includes an aspiration needle that is insertable through the third port and passageway of the needle guide and extendable beyond the distal end of the suction tube to puncture and aspirate the ovarian cyst. A check valve is also connected to the proximal end of the aspiration needle to prevent suction of fluid within the aspiration needle from being drawn therefrom and through the passageway of the suction tube. A sealing cap is likewise positioned about the third port for maintaining purchase of the ovarian cyst and suction tube prior to and during insertion of the aspiration needle. The endoscopic instrument further includes a suction tube connectable to the second port for maintaining a vacuum within the suction tube. A clamp positioned about the connecting tube regulates the vacuum through the connecting and suction tube.

BRIEF DESCRIPTION OF THE DRAWING

FIG. 2 depicts a partial cross-sectional view of the endoscopic instrument of FIG. 1; and FIG. 3 depicts a view of the distal end of the endoscopic instrument along the line 3—3 of FIG. 2.

DETAILED DESCRIPTION

Figure 1:
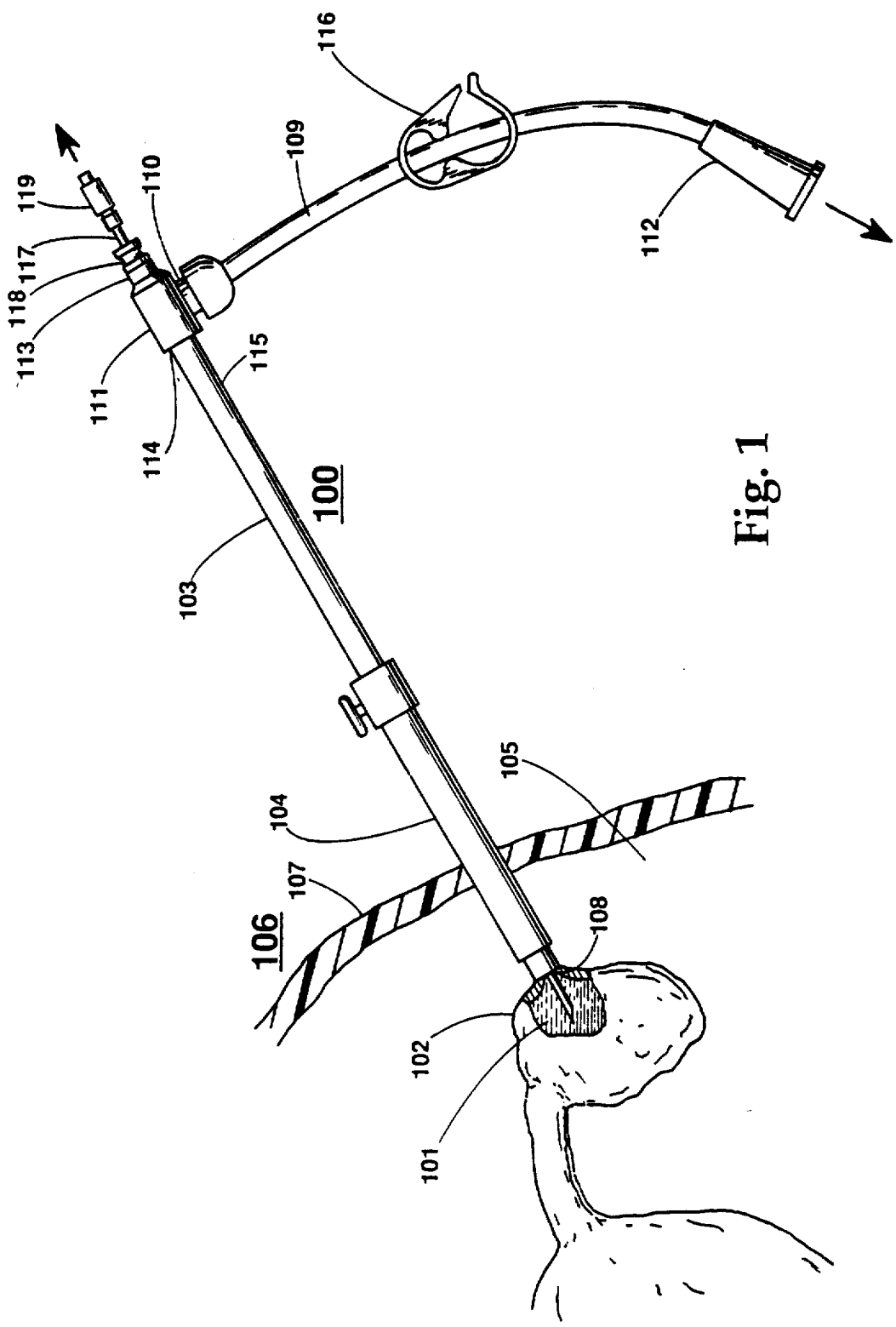
FIG. 1 depicts the endoscopic aspiration instrument of the present invention inserted through a trocar sheath into a patient.

Depicted in FIG. 1 is endoscopic instrument 100 such as a pelviscopic cyst aspirator for aspirating fluid 101 from an ovarian cyst 102. The instrument includes an elongated member 103 such as a stainless steel suction tube which is passed through the passageway of trocar sheath 104 and into the peritoneal cavity 105 of patient 106. The trocar sheath is inserted through the abdominal wall 107 of a patient for performing a minimally invasive laparoscopic or pelviscopic procedure usually associated with the reproductive organs of a female patient. The distal end 108 of the elongated suction tube member is positioned to engage the outer wall of the ovarian cyst and maintain purchase of the cyst by a vacuum introduced via suction connecting tube 109 attached to side port 110 of connector 111 and a vacuum source (not shown) attached to connector 112 of the connecting tube. T-type connector 111 has three ports 110, 113, and 114 of which the proximal end 115 of suction tube 103 is connected to access port 114. A well-known regulating clamp 116 is positioned about suction connecting tube 109 and regulates the amount of vacuum maintained on cyst 102. Aspiration needle 117 is inserted through sealing cap 118, access port 113, and suction tube 103 to puncture and aspirate the ovarian cyst. When inserted into the cyst, another source of vacuum is applied to the proximal end of the aspiration needle through one-way check valve 119 to aspirate fluid 101 without leaking into peritoneal cavity 105.

Depicted in FIG. 2 is a cross-sectional view of endoscopic instrument 100 with aspiration needle 117 positioned for insertion through sealing cap 118 and into access port 113. Endoscopic instrument 100 basically comprises elongated suction tube member 103, connector 111, and a second elongated needle guide member 120 interconnected as shown. By way of example, elongated suction tube member 103 comprises a type 302 stainless steel tube approximately 31 cm in length. The suction tube includes a hollow passageway 121 approximately ⅜" in diameter and wall 122 approximately 0.035" in thickness. Distal end 108 of the tube engages and maintains purchase of the ovarian cyst with the aid of a vacuum applied through passageway 121 and connector 111. Proximal end 115 of the suction tube is connected to the first port 114 of the connector with the aid of a well-known threaded interconnection.

Second elongated member 120, referred to as an aspiration needle guide, is centrally positioned within passageway 121 of suction tube 103. By way of example, needle guide 120 is approximately 40 cm long and comprises a 15 gauge thin wall tube having an outside diameter of approximately 0.072" and an internal passageway having an inside diameter of 0.059" between distal end 124 and proximal end 125. The proximal end 125 extends centrally through first access port 114 of connector 111 and connects to second access port 113 as shown with the use of well-known silver solder to secure the proximal end to the access port. Positioning device 126 is positioned about the distal end of the needle guide to center the needle guide within passageway 121 of the suction tube.

Depicted in FIG. 3 is an end view of suction tube 103, needle guide 120, and positioning device 126 taken along the line 3—3 of FIG. 2. Positioning device 126 comprises a hollow sleeve 127 connected to distal end 124 of needle guide 120 using, for example, well-known silver solder. A plurality of arms 128 extends radially from sleeve 127 for centering needle guide 120 within passageway 121 of the suction tube. The ends of the arms make contact with the inside surface of tubular wall 12 to center needle guide 120 within passageway 121 of the suction tube. This allows the suction tube to be removed from the connector for cleaning. The positioning device is also located a predetermined distance from the distal end 108 of suction tube 103 for preventing the engaged ovarian cyst from being drawn too far into the suction tube.

Referring again to FIG. 2, connector 111 resembles a T-type fitting having three access ports 110, 113, and 114. The main body 129 of the connector is approximately 1¼" in length between directly opposed access ports 113 and 114. The outside diameter of the main body near first access port 114 is approximately 0.625". The main body also includes an inside cylindrical passageway 130 approximately 0.312" in diameter. Proximal end 115 and access port 114 are threaded to provide ready interconnection of the two components. Passageway 130 tapers to a diameter of 0.111" at the proximal end thereof for receiving the proximal end of needle guide 120. Similarly, the outside diameter of the main body of the connector reduces to an outside diameter of approximately 0.375". The proximal end of the main body includes a circular flange 131 for well-known sealing cap 118 to engage and provide an air-tight seal. Sealing cap 118 is commercially available from Cook Urological, Inc., Spencer, Ind. Proximal end 125 of needle guide 120 is connected to access port 113 using well-known silver solder.

Side access port 110 opens into main connector passageway 130 via connecting tube adaptor 132 having an outside diameter of approximately 0.495" and an internal passageway 133 having a diameter of approximately 0.250". Connecting tube adaptor 132 is either silver-soldered or press-fit into the main body of connector 111. Vacuum connecting tube 109 connects between adaptor 132 and vacuum suction equipment (not shown) to provide vacuum and aspiration through access port 110 and passageway 121 of suction tube 103. Well-known connecting cap 134 secures connecting tube 109 to adaptor 132 and access port 110.

When the suction tube 103 is placed next to an ovarian cyst wall, suction applied through connecting tube 109 and passageway 121 draws the ovarian cyst wall into the end of suction tube 103 up to positioning device 126. In addition, the ovarian cyst wall is engaged against the distal end 124 of needle aspiration guide 120.

Aspiration needle 117 is a well-known aspiration needle approximately 40 cm in length and is comprised of either a 14 or 17 gauge metal tube with a hub connector 135 at the proximal end thereof. A standard lancet bevel is provided at the distal end 136 of the tube. A well-known one-way check valve 137 is connected to the proximal end of the hub typically with a well-known Luer lock connector. A second source of vacuum or suction is applied to proximal end 138 for providing suction to aspirate fluid from the ovarian cyst through the tube of the aspiration needle.

To briefly describe the procedure utilized with the cyst aspiration instrument, the aspirating needle 117 is inserted through sealing cap 118, access port 113, and into passageway 123 of the needle guide 120. Suction is applied to the distal end 138 of the check valve. The instrument is then inserted into the peritoneal cavity through the trocar sheath 104 as shown in FIG. 1. Suction via connecting tube 109 is applied to passageway 121 of suction tube 103, which engages the outside wall of the ovarian cyst. Sufficient purchase is maintained to manipulate the cyst and the ovary, if necessary. Well-known regulating clamp 116 is in a generally full open position for maximum purchase. The aspiration needle is then extended through the needle guide to puncture the wall of the cyst. Fluid from the cyst is drawn through the aspiration needle to aspirate and deflate the cyst. A saline lavage is also utilized with the aspirating needle to further aspirate or evacuate the cystic contents. The one-way check valve 137 prevents fluid from flowing back through the needle and into suction tube 103. Should any fluid leak from about the outer wall of the aspiration needle, suction tube 103 aspirates any emerging fluid.

The aspiration needle is removed, and the cyst is fully deflated by aspiration through suction tube 103. Purchase of the cyst wall is maintained within suction tube 103 and positioning device 128. The surgeon then employs a well-known tying off technique of the ruptured cyst end, and the cyst is removed using well-known surgical techniques.

Suction is maintained while the aspirating instrument is withdrawn from the cavity. This is done to prevent any backward draining or leakage of fluid down the shaft. The aspiration instrument is then removed without any leakage or drainage of possibly malignant cells into the peritoneal cavity. As a result, the leakage of possibly malignant cyst fluid into the peritoneal cavity during a minimally invasive pelviscopic procedure is minimized if not completely eliminated.

It is to be understood that the above-described medical instrument for aspirating a cyst without fluid leakage is merely an illustrative embodiment of the principles of this invention and that other apparatus may be devised by those skilled in the art without departing from the spirit and scope of this invention. In particular, the endoscopic instrument is comprised of basically three components consisting of a suction tube, a needle guide and a connector with three access ports. Alternatively, the suction tube can be provided with a single, side access port and a second access port at the proximal end for inserting the aspiration needle therethrough. The centering device may be attached to the distal end of the suction tube without the need for the needle guide. In this embodiment, the aspiration needle is inserted through the sealing cap and the second access port at the proximal end of the suction tube and centered by the physician for insertion into the cyst through positioning device 128. Although described for aspirating an ovarian cyst, the aspiration instrument may also be utilized to aspirate bile from the gallbladder, fluid from kidney cysts, or fluid from other cavities of the body.

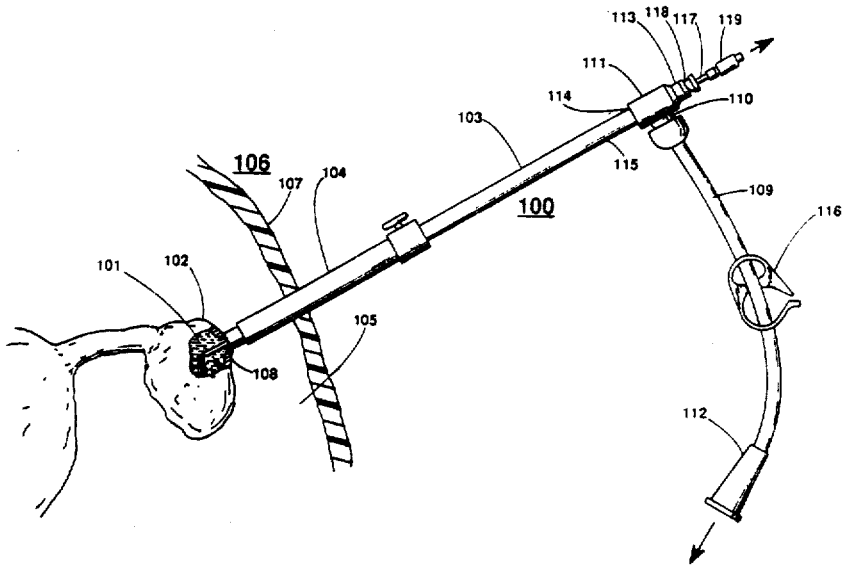

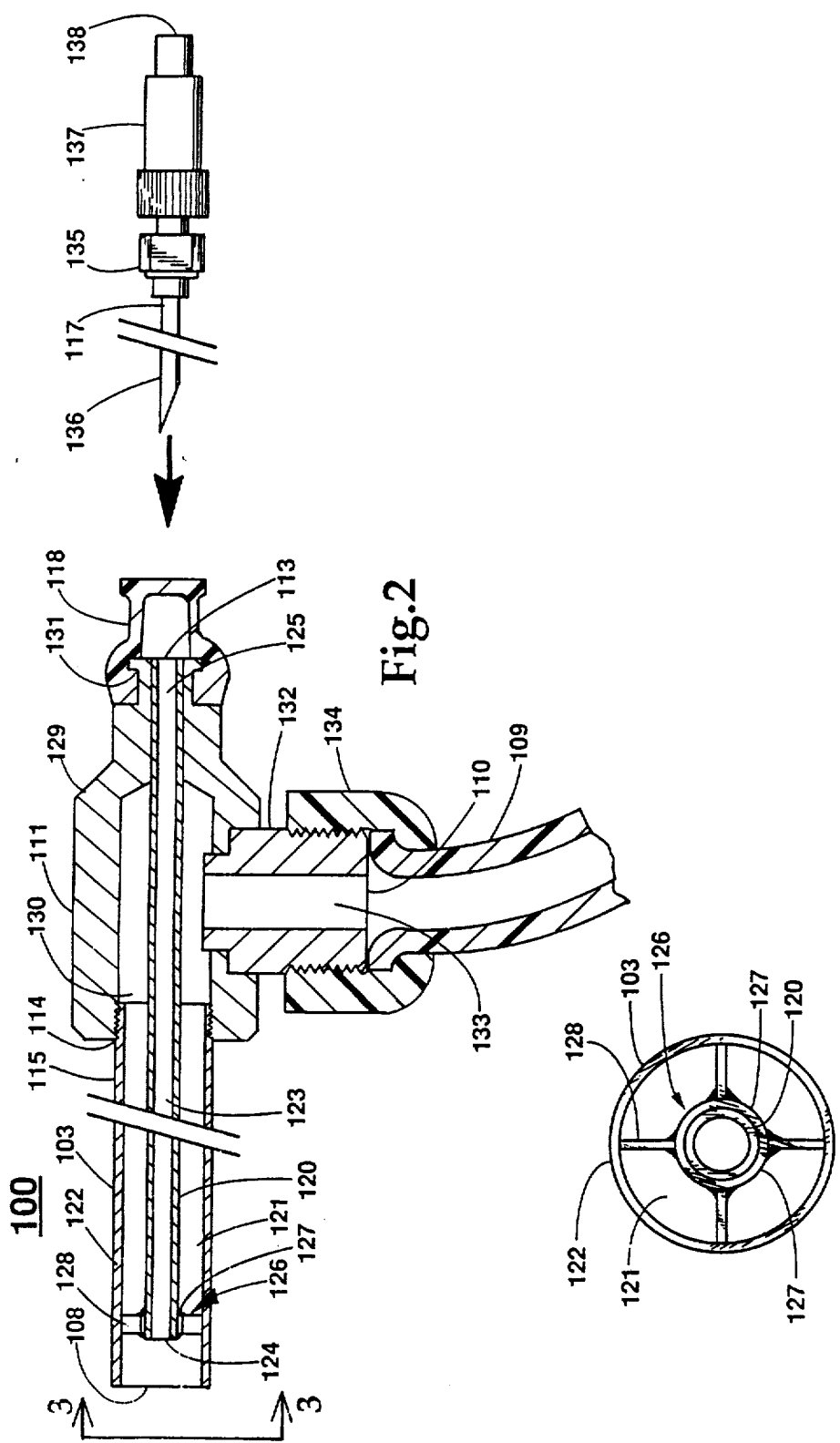

What is claimed is:

1. An endoscopic instrument comprising:
   a first elongated member having a first distal end, a first proximal end, and a first longitudinal passageway extending between said first ends, said first proximal end having first and second access ports, said first access port having access to said first passageway; and
   a positioning device positioned within said first passageway a predetermined distance from said first distal end and having a positioning passageway capable of receiving an aspiration needle inserted through said second access port.

2. The endoscopic instrument of claim 1 further comprising a second elongated member having a second distal end, a second proximal end, and a second longitudinal passageway extending between said second ends, said positioning device positioned about said second distal end of said second member, said second proximal end connected to said second access port, and said second access port having access to said second passageway.

3. The endoscopic instrument of claim 2 further comprising a sealing cap positioned over said second access port.

4. The endoscopic instrument of claim 2 further comprising said aspiration needle insertable through said second access port and said second member and extendable beyond said first distal end of said first elongate member.

5. The endoscopic instrument of claim 4 further comprising a check valve connected to a proximal end of said aspiration needle.

6. The endoscopic instrument of claim 1 further comprising a suction connecting tube attached to said first port and a regulating clamp positioned about said suction tube.

7. The endoscopic instrument of claim 1 wherein said first member comprises a tube having an outer surface with a predetermined finish about said first distal end.

8. An endoscopic instrument comprising:
   a first elongated member having a first distal end, a first proximal end, and a first longitudinal passageway extending between said first ends, said first proximal end having first and second access ports, said first access port having access to said first passageway; and
   a second elongated member positioned within said first passageway and having a second distal end, a second proximal end, and a second longitudinal passageway extending between said second ends, said second proximal end connected to said second access port, and said second access port having access to said second passageway.

9. The endoscopic instrument of claim 8 further comprising a positioning device attached about said second distal end of said second member and positioned within said first passageway a predetermined distance from said first distal end of said member.

10. An endoscopic instrument comprising:
    a connector having first, second, and third access ports;
    a first elongated member having a first distal end, a first proximal end connected to said first access port, and a first longitudinal passageway extending between said first ends and accessible through said second port; and
    a second elongated member positioned within said first passageway and through said first port and having a second distal end, a second proximal end connected to said third access port, and a second longitudinal passageway extending between said second ends and accessible through said third port.

11. The endoscopic instrument of claim 10 further comprising a positioning device attached about said second distal end of said second member and positionable within said first passageway of said first member.

12. The endoscopic instrument of claim 11 wherein said positioning device comprises a sleeve positionable around said second distal end of said second member and a plurality of arms extending radially from said sleeve toward said first member.

13. The endoscopic instrument of claim 11 wherein said positioning device is positioned a predetermined distance from said first distal end of said first member when said first member is connected to said first port of said connector.

14. The endoscopic instrument of claim 10 wherein said first member has an outer surface having a predetermined finish about said first distal end thereof.

15. The endoscopic instrument of claim 10 further comprising an aspiration needle insertable through said third port and said second passageway of said second member.

16. The endoscopic instrument of claim 15 wherein said aspirating needle has a one-way check valve attached to a proximal end thereof.

17. The endoscopic instrument of claim 10 further comprising a pliable material sealing cap positioned about said third port of said connector.

18. The endoscopic instrument of claim 10 further comprising a suction connecting tube connectable to said second port.

19. The endoscopic instrument of claim 18 further comprising a clamp positioned about said suction connecting tube.

20. A laparoscopic instrument for aspirating a cyst comprising:
    a connector having first, second, and third access ports;
    a suction tube having a first distal end, a first proximal end, and a first hollow longitudinal passageway extending therebetween, said first proximal end being connected to first port of said connector, said second access port having access to said first passageway, said suction tube having an outside surface with a non-glare finish about said first distal end;
    a needle guide having a second distal end, a second proximal end, and a second hollow longitudinal passageway extending therebetween and positioned within said first passageway of said suction tube, said second proximal end extending through said first access port and being connected to said third access port of said connector, said third access port having access to said second passageway of said needle guide;

a centering device having a sleeve attached about said second distal end of said needle guide a predetermined distance from said first distal end of said suction tube and also having a plurality of arms radially extending from said sleeve to and making contact with an inside surface of said suction tube;

a puncturable sealing cap positioned over said third access port;

a suction connecting tube connected to said second access port of said connector;

a suction regulating clamp positioned about said suction tube;

an aspiration needle extendable through said sealing cap, said third access port, said needle guide, and beyond said first distal end of said suction tube; and a one-way valve connected to a proximal end of said aspirating needle.

* * * * *

UNITED STATES PATENT AND TRADEMARK OFFICE
CERTIFICATE OF CORRECTION

PATENT NO. : 4,958,621

DATED : September 25, 1990

INVENTOR(S) : Howard C. Topel, Thomas L. Foster

It is certified that error appears in the above-identified patent and that said Letters Patent is hereby corrected as shown below:

The title page should be deleted to appear as per attached title page. The two sheets of drawing consisting of figures 1-3 should be added as shown on the attached sheets.

Signed and Sealed this

Thirtieth Day of April, 1991

Attest:

HARRY F. MANBECK, JR.

Attesting Officer

Commissioner of Patents and Trademarks

United States Patent [19]

Topel et al.

[11] Patent Number: 4,958,621

[45] Date of Patent: Sep. 25, 1990

[54] ENDOSCOPIC ASPIRATION INSTRUMENT

[75] Inventors: Howard C. Topel, Deerfield, Ill.; Thomas L. Foster, Poland, Ind.

[73] Assignee: Vance Products Incorporated, Spencer, Ind.

[21] Appl. No.: 505,082

[22] Filed: Apr. 4, 1990

[51] Int. Cl.$^5$ ............................................. A61B 1/00
[52] U.S. Cl. ............................................................ 128/4
[58] Field of Search ............................................ 128/4, 6

[56] References Cited

U.S. PATENT DOCUMENTS

| | | | |
|---|---|---|---|
| 4,653,475 | 3/1987 | Seike et al. | 128/4 |
| 4,686,965 | 8/1987 | Bonnet et al. | 128/4 |
| 4,700,694 | 10/1987 | Shisido | 128/4 X |

OTHER PUBLICATIONS

American Surgical Instruments, Inc., "Nezhat-Dorsey Disposable Hydro-Dissection Trumpet Valve," 3 Sheets, received Mar. 19, 1990.
K. Semm, Pelviscopy Operative Guidelines, Kiel, F.R.G., 1988, pp. 53-54.
Storz The World of Endoscopy, Semm Instruments for Operative Pelviscopy, 4th Edition, Mar., 1987.

*Primary Examiner*—William H. Grieb
*Attorney, Agent, or Firm*—Richard J. Godlewski

[57] ABSTRACT

An endoscopic aspiration instrument suitable for use with a trocar sheath in laparoscopic surgical procedures is disclosed for aspirating fluid from an ovarian cyst without leakage of the fluid into the peritoneal cavity. The endoscopic instrument comprises a elongated suction tube member having a needle guide positioned within the passageway thereof. The suction tube and needle guide are connected at the proximal ends thereof with the use of a three access port connector. The first access port connects to the proximal end of the suction tube. The proximal end of the needle guide tube is extended through the first port and connected to the second port of the T-type connector. An aspiration needle is inserted through a sealing cap positioned over the second access port and into the passageway of the needle guide tube. A centering device comprising a sleeve and a plurality of radially extending arms is positioned about the distal end of the needle guide tube for centering the needle guide tube within the passageway of the suction tube. The centering device is also located a predetermined distance from the distal end of the suction tube for preventing the ovarian cyst from being drawn too far into the suction tube. The connector also includes a third side port for connection to suction equipment for providing a vacuum in the suction tube to engage the ovarian cyst.

20 Claims, 2 Drawing Sheets